(12) United States Patent
Felix et al.

(10) Patent No.: US 7,712,384 B2
(45) Date of Patent: May 11, 2010

(54) APPARATUS AND METHOD FOR MAINTAINING MULTI-COMPONENT SAMPLE GAS CONSTITUENTS IN VAPOR PHASE DURING SAMPLE EXTRACTION AND COOLING

(75) Inventors: Larry Gordon Felix, Pelham, AL (US); William Earl Farthing, Pinson, AL (US); James Hodges Irvin, Birmingham, AL (US); Todd Robert Snyder, Birmingham, AL (US)

(73) Assignee: Gas Technology Institute, Des Plaines, IL (US)

( * ) Notice: Subject to any disclaimer, the term of this patent is extended or adjusted under 35 U.S.C. 154(b) by 559 days.

(21) Appl. No.: 11/712,042

(22) Filed: Feb. 28, 2007

(65) Prior Publication Data

US 2008/0202261 A1 Aug. 28, 2008

(51) Int. Cl.
*G01N 1/00* (2006.01)

(52) U.S. Cl. .................................. 73/863.21
(58) Field of Classification Search .............. None
See application file for complete search history.

(56) References Cited

U.S. PATENT DOCUMENTS

| 4,974,455 | A | * | 12/1990 | McGowan et al. | 73/863.12 |
| 5,109,708 | A | * | 5/1992 | Lawless | 73/863.11 |
| 5,297,432 | A | * | 3/1994 | Traina et al. | 73/864.34 |
| 2006/0130599 | A1 | * | 6/2006 | Graze, Jr. | 73/864.73 |

* cited by examiner

*Primary Examiner*—Robert R Raevis
(74) *Attorney, Agent, or Firm*—Mark E. Fejer

(57) ABSTRACT

A dilution apparatus for diluting a gas sample. The apparatus includes a sample gas conduit having a sample gas inlet end and a diluted sample gas outlet end, and a sample gas flow restricting orifice disposed proximate the sample gas inlet end connected with the sample gas conduit and providing fluid communication between the exterior and the interior of the sample gas conduit. A diluted sample gas conduit is provided within the sample gas conduit having a mixing end with a mixing space inlet opening disposed proximate the sample gas inlet end, thereby forming an annular space between the sample gas conduit and the diluted sample gas conduit. The mixing end of the diluted sample gas conduit is disposed at a distance from the sample gas flow restricting orifice. A dilution gas source connected with the sample gas inlet end of the sample gas conduit is provided for introducing a dilution gas into the annular space, and a filter is provided for filtering the sample gas. The apparatus is particularly suited for diluting heated sample gases containing one or more condensable components.

14 Claims, 4 Drawing Sheets

APPARATUS AND METHOD FOR MAINTAINING MULTI-COMPONENT SAMPLE GAS CONSTITUENTS IN VAPOR PHASE DURING SAMPLE EXTRACTION AND COOLING

The U.S. Government has a paid-up license in this invention and the right in limited circumstances to require the patent owner to license others on reasonable terms as provided for by the terms of Contract No. DE-FC36-03G013175 awarded by the U.S. Department of Energy.

BACKGROUND OF THE INVENTION

1. Field of the Invention

This invention relates to a method and apparatus for diluting gaseous streams using a dilution gas. This invention further relates to a method and apparatus for maintaining multi-component sample gas constituents of a gaseous process stream in vapor phase so as to enable on-line characterization of these streams. This invention further relates to a method and apparatus for reducing the pressure and/or temperature of a stream extracted from a high pressure and/or high temperature industrial process so that condensable constituents in the unconditioned gas stream remain in the vapor phase and can be evaluated by standard process control instrumentation. Finally, this invention relates to a specialized sample gas dilution apparatus that has been designed and modeled to provide uniform, precise levels of sample gas dilution and/or cooling.

2. Description of Related Art

Gaseous process streams, such as those produced by synthesis gas production processes (e.g. coal, biomass and waste gasification), typically contain a significant proportion of vapor phase hydrocarbon species with dew points, at ambient pressures or above, that range from ambient temperature to process temperature. These gaseous process streams are often obtained at elevated conditions of pressure and/or temperature that exceed the operating limits of instruments available to perform on-line characterizations of these streams. In cases where on-line analysis is deemed necessary, representative sample streams must be extracted from the process and their pressure and/or temperature reduced to levels acceptable for these instruments. For some applications, difficulties and uncertainties in modifying the sample streams to conditions acceptable to on-line analyzers result in reliance on batch analyses performed on purposely condensed samples that are collected for remote laboratory analysis. Although batch sampling followed by remote analysis is often a simpler approach, results are delayed, and in cases where portions of the collected sample may be lost or chemically altered during collection, storage, and laboratory analysis procedures, this approach also may not be quantitatively or qualitatively accurate.

One conventional method for conditioning high temperature and/or high pressure gaseous process streams for analysis by analytical instrumentation is the use of syngas sampling trains in which depressurized syngas is passed through liquid impingers to trap and condense essentially all of the vapor-phase components in a suitable liquid carrier for subsequent analysis. When impingers are employed, the hot process gas may need to be cooled before it can be passed to the impinger train. Direct-contact heat exchangers are typically employed for this purpose and directly precede the impinger train. They are designed so that effective, intimate contact of the hot gas with cooled surfaces is maintained. The inherent weakness in this approach for syngas conditioning emerges when the gas is cooled to a temperature that is below the local dew point of one or more of its constituents (the dew points of water and hydrocarbon vapors are primarily determined by their local partial pressure within a heat exchanger). At the moisture and hydrocarbon species concentrations commonly found in gasifier process streams, transitions through these dew points are always encountered as the synthesis gas is cooled to ambient temperature. Thus, when using this conventional approach, some constituents of the process gas stream will always condense. When a dew point is reached, the water and/or at least a portion of the hydrocarbon species (tars, oils) condense and collect on cool surfaces. This condensation can degrade the efficiency of the heat exchanger, create cleanup, maintenance, and health issues, and provide the opportunity for free radicals and acids in the condensed vapors to react and change in structure and concentration before analyses can be carried out. These tars and oils can also be challenging to remove from sample lines and traps.

For on-line analyses of gaseous process streams, a significant reduction of the temperature of an extracted gas sample stream is often required because the upper temperature limit of the on-line instrument(s) is often well below the lowest process temperature. Likewise, the pressure of the extracted sample stream may often be significantly reduced before it can be safely conveyed to the analyzer. Conventional pressure-reducing valves or orifices are commonly used to reduce gas pressures, and conventional contact heat exchangers are frequently used to reduce gas temperatures. However, as a gas sample cools, the potential for the condensation of vapor-phase components increases, particularly when interior portions of the heat exchanger are locally cooler than the condensation temperature for one or more of the constituents of the gas sample. As previously indicated, depending on the process and the analytical instruments used to characterize the process, the loss of vapor-phase constituents by condensation can result in plugged sample lines, delayed or inaccurate measurements, and failure of the gas analyzers. For this reason, syngas analyses have generally been limited to batch sample extraction methods that include built-in traps or reservoirs for collecting condensed hydrocarbons, with the attendant difficulties previously described.

Accordingly, it is apparent that a better approach is needed to manage sample gas conditioning of gasification process streams to avoid condensation so that standard gas analyzers can be employed to quantify the various components of these gases.

SUMMARY OF THE INVENTION

It is, thus, one object of this invention to provide a method and apparatus for enabling the on-line characterization of gaseous process streams, such as synthesis gas (syngas) streams from gasification processes.

It is one object of this invention to provide a method and apparatus for maintaining condensable constituents of multi-component sample gases in a vapor phase during sample extraction and cooling.

It is another object of this invention to provide a method and apparatus for managing the cooling and dilution of gas streams extracted from high-temperature industrial process streams so that condensable constituents in the extracted stream are maintained as a gas while it is cooled and diluted to an arbitrary temperature lower than that of the process stream.

It is a further object of this invention to provide an apparatus for uniformly diluting and/or cooling gaseous streams.

It is a further object of this invention to provide an apparatus for uniformly diluting and/or cooling a gas stream extracted from a high temperature and/or high pressure industrial process.

These and other objects of this invention are addressed by an apparatus for diluting a gas sample comprising a sample gas conduit having a sample gas inlet end and a diluted sample gas outlet end. An orifice plate having a sample gas flow restricting orifice, disposed proximate the sample gas inlet end, is connected with the sample gas conduit, providing fluid communication between the exterior and the interior of the sample gas conduit. A diluted sample gas conduit is disposed within the sample gas conduit. The diluted sample gas conduit has a mixing end with a mixing space inlet opening disposed proximate the sample gas inlet end at a distance from the sample gas flow restricting orifice and forms an annular space between the sample gas conduit and the diluted sample gas conduit. Dilution gas means are provided for introducing a dilution gas into the annular space, and filter means connected with the sample gas inlet end of the sample gas conduit are provided for filtering the heated sample gas. In accordance with one embodiment of this invention, the filter means comprises a porous filter. A dedicated purge or calibration gas line is provided through which a purge or calibration gas may be directed to provide a calibration standard or spike and to clean the porous filter when particulate matter accumulates on the surface of the porous filter and an unacceptable pressure develops across the filter.

One of the significant benefits of providing a condensate-free gas to a suite of gas analysis equipment is that it provides the ability to assess the performance of high-temperature and/or high-pressure industrial processes on a real-time basis so that process efficiency and economy can be suitably controlled. The apparatus is particularly suitable for operating in a high-pressure environment, although high differential pressures are not required for the apparatus to function properly. Only a pressure difference sufficient to force the particle-free gas through the flow restricting orifice and maintain proper downstream flow is necessary. Likewise, this apparatus can function equally well at high and low process temperatures. Of critical importance is the requirement of sufficient gas volume flow to ensure thorough, turbulent mixing of dilution gas with a fully-relaxed jet of depressurized, undiluted gas. It should be noted that calibration gases may be used with or in place of dilution gas.

In operation, a particle-free gas at concentration $C_0$, pressure $P_0$, and temperature $T_0$ is expanded to a lower pressure through a flow restricting orifice of diameter D, emerging at pressure $P_1$ and temperature $T_1$. The expanded particle-free gas is mixed with a dilution gas at a temperature $T_2$ and pressure $P_2$ flowing through the annular space of the apparatus at flow rate $Q_2$. The dilution gas is turbulently mixed with the particle-free gas that has passed through the flow restricting orifice, creating a diluted gas concentration $C_1$ at pressure $P_3$ and temperature $T_3$ flowing at a rate $Q_3$.

BRIEF DESCRIPTION OF THE DRAWINGS

These and other objects and features of this invention will be better understood from the following detailed description taken in conjunction with the drawings, wherein.

DETAILED DESCRIPTION OF THE PRESENTLY PREFERRED EMBODIMENTS

The invention disclosed and claimed herein is an apparatus and method for enabling real-time process control in high temperature and/or high-pressure processes where the evaluation of sample gases extracted from the processes has heretofore not been possible in real-time due to the difficulty in conveying a representative gas sample from the process to an appropriate analyzer. Currently, the only reliable approach that allows for the assessment of the effluent generated by high-pressure and/or high-temperature gasification processes is through laborious batch sampling procedures that attempt to collect all of the condensable constituents in a stream extracted from the process for subsequent laboratory analysis. Because the analyses of the condensed gas constituents must occur some time after the samples are collected, the opportunity exists for free radicals and acids in the condensed vapors to react and change in structure and concentration before analyses can be completed. These tars and oils can plug sampling lines and be challenging to remove from the sample lines and traps. Thus, in order to manage high temperature and/or high-pressure industrial processes, an approach is needed to provide for the real-time characterization of the gaseous effluents generated by these processes.

It will, however, be appreciated by those skilled in the art that the apparatus and method of this invention may be applied to any gaseous stream requiring dilution and/or cooling. In addition, the apparatus of this invention may also be used for diluting gases at ambient process pressures or below by drawing a vacuum on the apparatus while managing the dilution gases.

Figure 1:
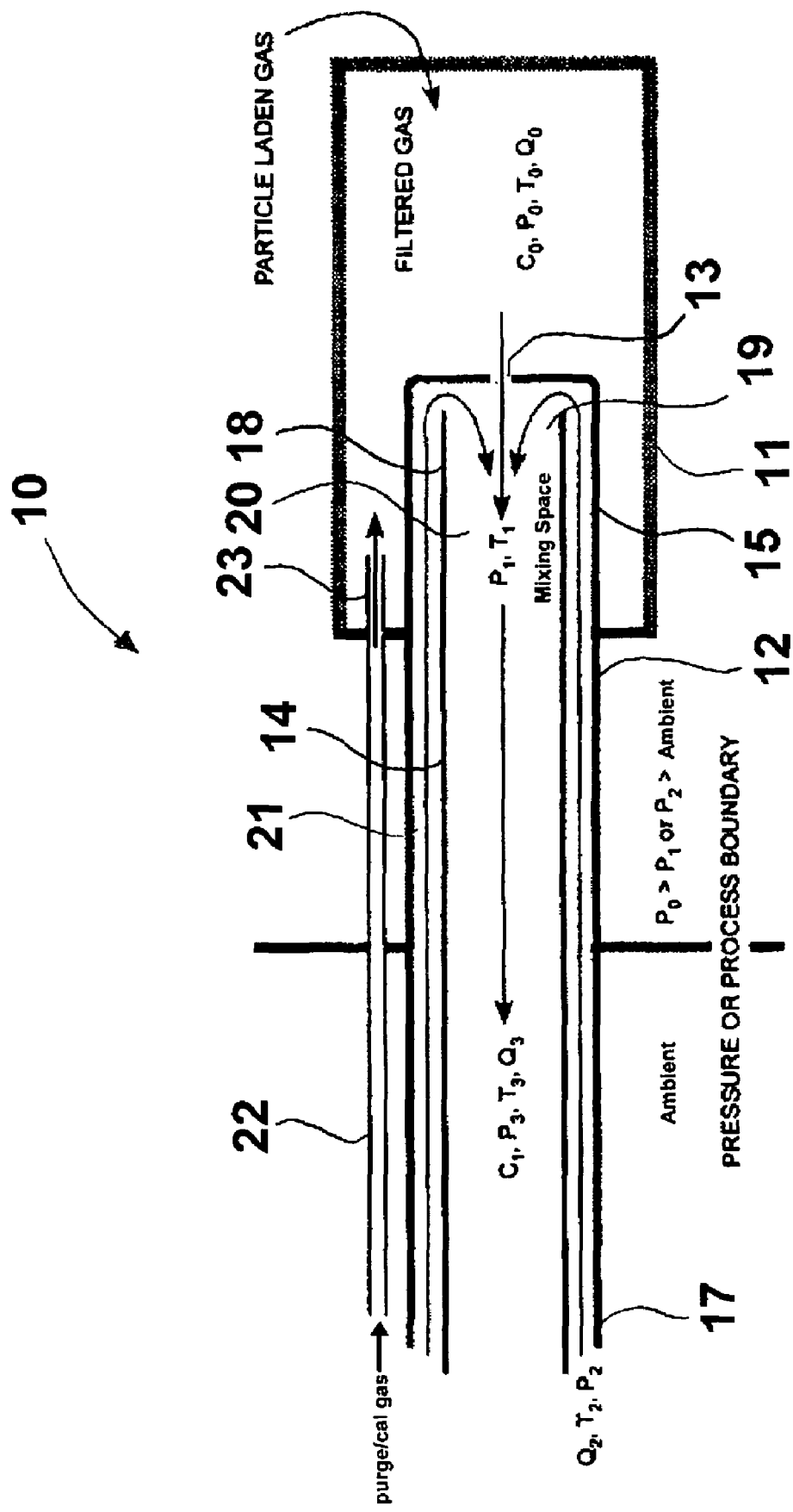
FIG. 1 is a side view diagram of a gas dilution device in accordance with one embodiment of this invention.

FIG. 1 is a diagram of a dilution apparatus in accordance with one embodiment of this invention. Dilution apparatus 10 comprises sample gas conduit 12 having a sample gas conduit inlet end 15 and a sample gas conduit outlet end 17. An orifice plate forming flow restricting orifice 13, which is axially aligned along the longitudinal axis of the apparatus, is connected with sample gas conduit 12 proximate sample gas conduit inlet end 15. In accordance with one preferred embodiment of this invention, particularly suitable for use in high pressure processes, flow restricting orifice 13 is a critical orifice. Disposed within sample gas conduit 12 is diluted sample gas conduit 14 having diluted sample gas conduit inlet end 18 with diluted sample gas conduit inlet opening 19. Disposed between sample gas conduit 12 and diluted sample gas conduit 18 is annular space 21 through which a dilution gas is introduced into diluted sample gas conduit 14. As shown in FIG. 1, dilution gas flows through annular space 21 in the direction of diluted sample gas conduit inlet end 18. To enable dilution gas to enter diluted sample gas conduit 14 through diluted sample gas conduit opening 19, the diluted sample gas conduit inlet end 18 is disposed at a distance, i.e. downstream, from flow restricting orifice 13. Thus, sample gas entering sample gas conduit 12 through flow restricting orifice 13 mixes with dilution gas entering diluted sample gas conduit 14 in mixing space 20 disposed proximate diluted sample gas conduit inlet end 18 of diluted sample gas conduit 14. The dilution gas may be lower, equal to, or greater in temperature than the sample gas expanding through flow restricting orifice 13. The rate of turbulent mixing may be adjusted either by manipulating the dilution gas flow rate or by moving diluted sample gas conduit 14 either closer to or further away from the flow restricting orifice.

Figure 2:
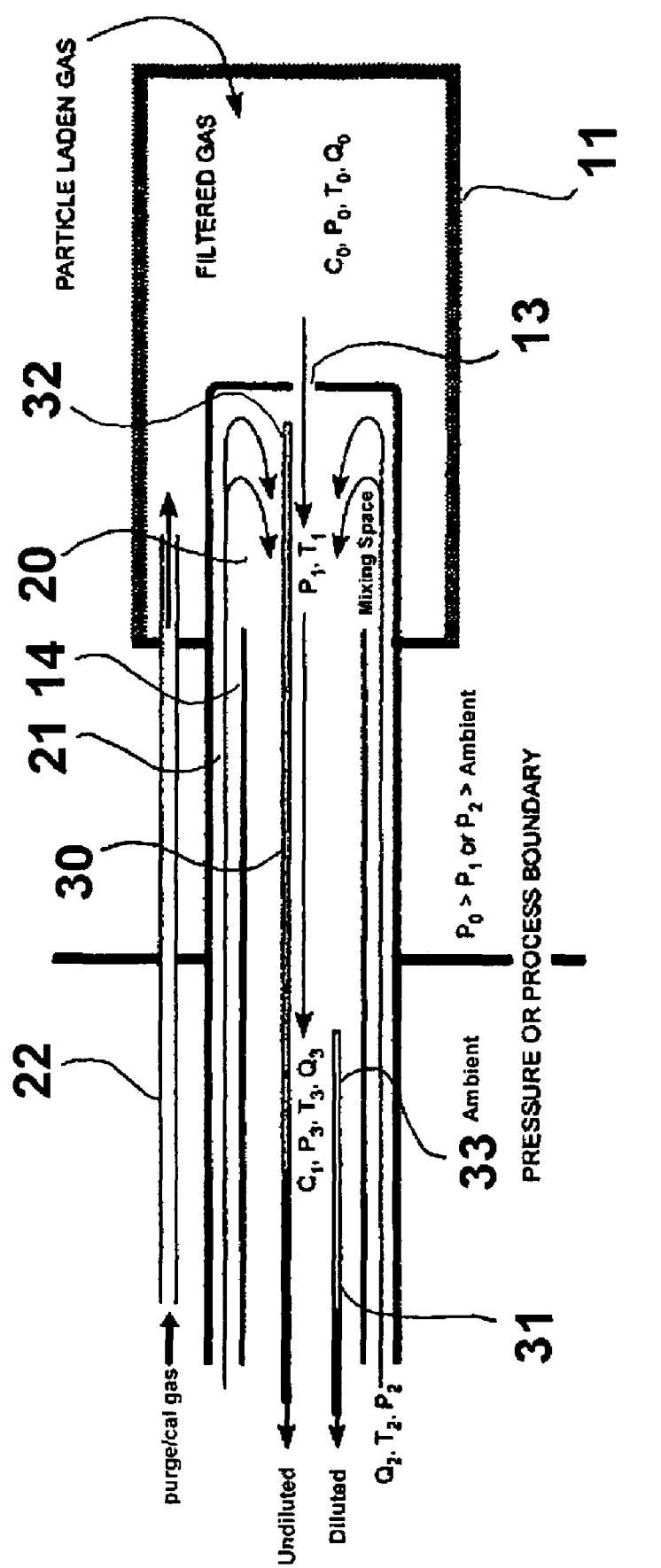
FIG. 2 is a side view diagram of a gas dilution device with capillary sampling tubes in accordance with one embodiment of this invention.

As shown in FIG. 2, by moving the diluted sample gas conduit inlet end away from flow restricting orifice 13, tube 30 disposed within diluted sample gas conduit 14 may be inserted into the process and its inlet end 32 may be positioned close to flow restricting orifice 13 so that a sample of the undiluted sample gas that has been expanded to a much lower pressure, $P_1$, may be withdrawn. In accordance with one embodiment of this invention, diluted sample gas tube 31 having diluted sample gas tube inlet end 33 is disposed within diluted sample gas conduit 14 with its inlet end disposed downstream of mixing space 20 for withdrawing a sample of diluted sample gas having concentration $C_1$. Samples of gas withdrawn through these tubes may be sent to mass spectrometers to measure the concentrations of various gas species. In accordance with one preferred embodiment of this invention, tubes 30 and 31 are capillary tubes.

Connected with sample gas conduit inlet end 15 in accordance with one embodiment of this invention is porous filter 11 for removal of particles in the sample gas prior to introduction into sample gas conduit 12. In accordance with one preferred embodiment of this invention for use in high-temperature applications, porous filter 11 is a passivated porous metal filter. In accordance with another preferred embodiment, porous filter 11 is an inert porous ceramic filter. As shown in FIG. 1, in accordance with one embodiment of this invention, porous filter 11 forms a chamber around sample gas conduit inlet end 15. Purge/calibration gas conduit 22 having purge/calibration gas outlet end 23 in fluid communication with the chamber provides a purge and/or calibration gas into the chamber as a means for cleaning porous filter 11 and providing an entry point for calibration or "spike" gas in close proximity to the process. In particular, short, high-pressure bursts of gas, heated or cooled to process temperature, may be directed through purge/calibration gas conduit 22 to clean the filter.

Figure 3:
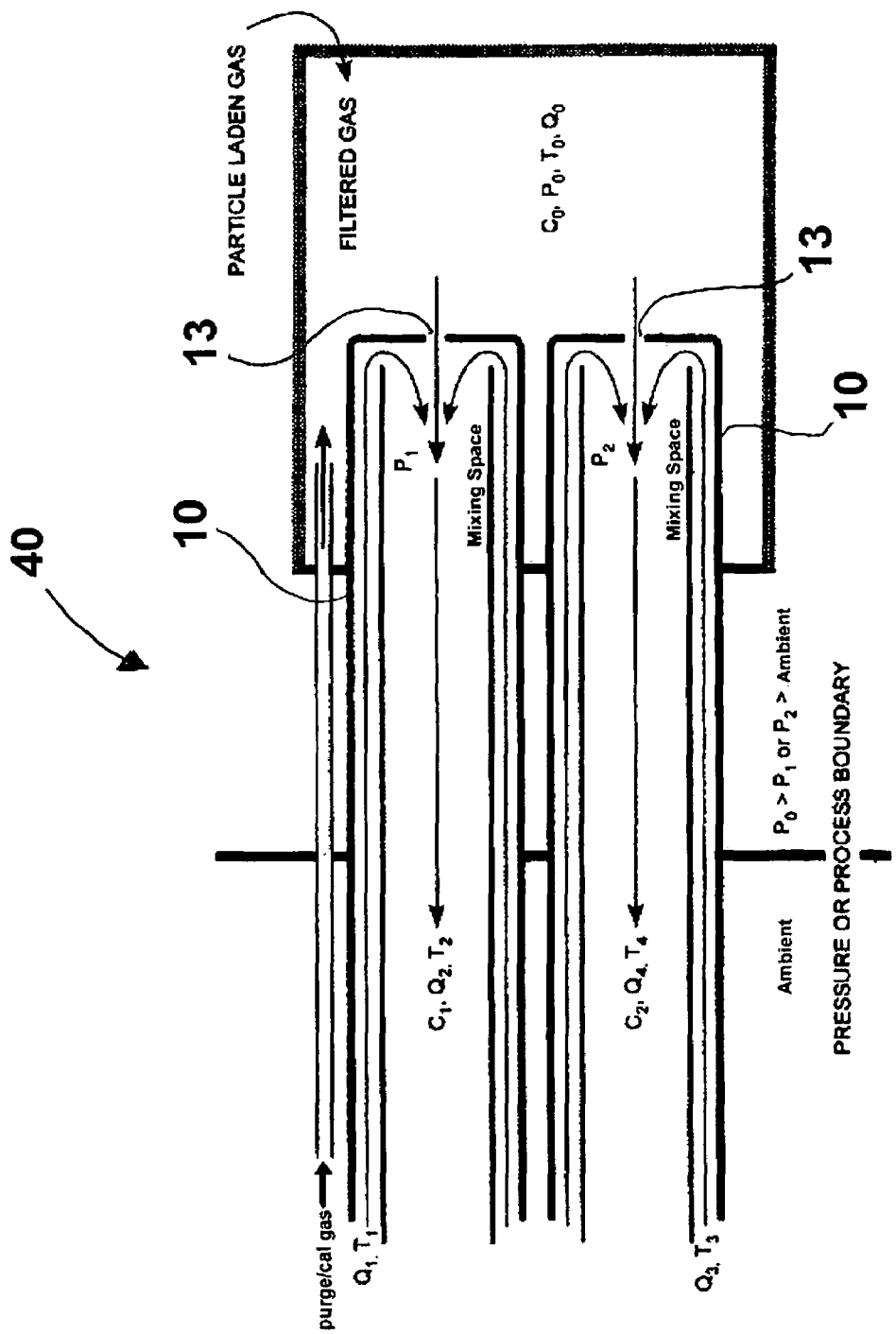
FIG. 3 is a side view diagram of a parallel arrangement of two gas dilution devices in accordance with one embodiment of this invention.

It will be apparent that the apparatus of this invention is a self-contained dilution apparatus. Consequently, a plurality of dilution apparatuses may be bundled to form aggregates of one or more apparatuses to create separate diluted gas streams. Such a bundle 40 employing two dilution apparatuses 10 is shown in FIG. 3.

Figure 4:
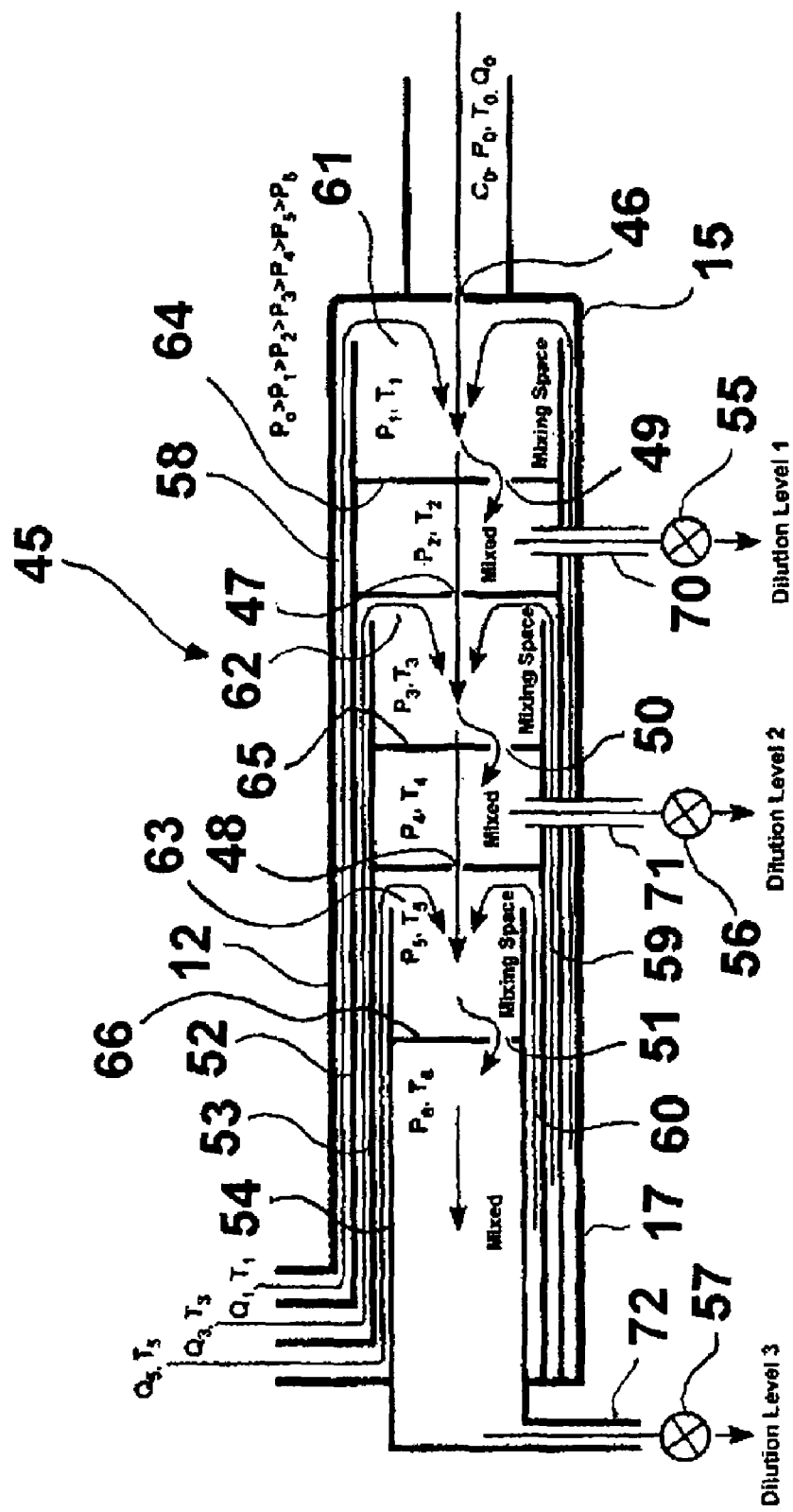
FIG. 4 is a side view diagram of a staged or cascaded arrangement of a gas dilution device in accordance with one embodiment of this invention.

FIG. 4 is a diagram showing a staged, or cascaded dilution apparatus 45 in accordance with one embodiment of this invention. As shown, the apparatus comprises a sample gas conduit 12 having an inlet end 15 with which a first stage orifice plate having a first stage flow restricting orifice 46 is connected. Disposed within sample gas conduit 12 is a first stage diluted sample gas conduit 52 having first stage diluted sample gas conduit inlet opening 61 and forming first stage annular space 58 between sample gas conduit 12 and first stage diluted sample gas conduit 52. A first stage mixing space wall 64 having a first stage mixing orifice 49 offset from the longitudinal axis of the apparatus is disposed within and connected with first stage diluted sample gas conduit 52 at a distance from first stage diluted sample gas conduit inlet opening 61, forming a first stage mixing space between the first stage mixing space wall 64 and first stage diluted sample gas conduit inlet opening 61.

Disposed within and connected with first stage diluted sample gas conduit 52 downstream of and at a distance from first stage mixing space wall 64 is a second stage orifice plate having a second stage flow restricting orifice 47, which is axially aligned with the first stage flow restricting orifice 46. A second stage diluted sample gas conduit 53 having a second stage diluted sample gas conduit inlet opening 62 at a distance from second stage flow restricting orifice 47 is disposed in first stage diluted sample gas conduit 52, forming a second stage annular space 59 between second stage diluted sample gas conduit 53 and first stage diluted sample gas conduit 52 through which dilution gas is introduced into the mixing space downstream of the second stage flow restricting orifice 47. A second stage mixing space wall 65 having a second stage mixing orifice 50 offset from the longitudinal axis of the apparatus is disposed within and connected with second stage diluted sample gas conduit 53 at a distance from second stage diluted sample gas conduit inlet opening 62, forming a second stage mixing space between the second stage mixing space wall 65 and second stage diluted sample gas conduit inlet opening 62.

Disposed within and connected with second stage diluted sample gas conduit 53 downstream of and at a distance from second stage mixing space wall 65 is a third stage orifice plate having a third stage flow restricting orifice 48, which is axially aligned with the first stage flow restricting orifice 46. A third stage diluted sample gas conduit 54 having a third stage diluted sample gas conduit inlet opening 63 at a distance from third stage flow restricting orifice 48 is disposed in second stage diluted sample gas conduit 53, forming a third stage annular space 60 between third stage diluted sample gas conduit 54 and second stage diluted sample gas conduit 53 through which dilution gas is introduced into the mixing space downstream of the third stage flow restricting orifice 48. A third stage mixing space wall 66 having a third stage mixing orifice 51 offset from the longitudinal axis of the apparatus is disposed within and connected with third stage diluted sample gas conduit 54 at a distance from third stage diluted sample gas conduit inlet opening 63, forming a third stage mixing space between the third stage mixing space wall 66 and third stage diluted sample gas conduit inlet opening 63.

As shown in FIG. 4, in accordance with one embodiment of this invention, a diluted sample gas withdrawal conduit 70, 71, 72 is provided for withdrawal of a diluted sample gas sample at each dilution level. The withdrawal of the gas samples may be regulated by regulating valves 55, 56, 57, respectively. As will be appreciated by those skilled in the art, for each stage through which the sample gas passes, the pressure in each stage will be lower than the pressure in the preceding stage and the dilution level in each stage will be higher than the dilution level in the preceding stage.

The method for maintaining multi-component sample gas constituents in a vapor phase during sample extraction and cooling in accordance with one embodiment of this invention comprises the essential steps of expansion of particle-free, undiluted process gas through an orifice, thereby forming a reduced pressure undiluted process gas, relaxation of the depressurized jet to approximate plug flow, and complete turbulent mixing of the undiluted, reduced pressure process gas with an inert diluting gas before being conveyed to a remotely situated suite of gas analysis instrumentation.

In environments in which contact of the walls and interior boundaries of the diluter assembly with undiluted gas can result in chemical reactions, catalytic reactions, or physical adsorption, the interior surfaces of the apparatus may be coated with a thin, inert film of silica, such as that provided by a RESTEK SILCOSTEEL® or SULFAINERT® coating to prevent such effects. Typical materials from which the apparatus of this invention may be constructed include 316L and 310 series stainless steels, and other high performance alloys, including FeCrAlloy, Haynes 260, and Inconel alloys. For low temperature applications with non-reactive gases, more inexpensive materials and methods of construction may be employed. In such cases, some internal parts may be constructed from injection-molded plastics or metals.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. An apparatus for diluting a gas sample, the apparatus comprising:
    a sample gas conduit having a sample gas inlet end and a diluted sample gas outlet end;
    an orifice plate forming a sample gas flow restricting orifice disposed proximate said sample gas inlet end connected with said sample gas conduit and providing fluid communication between an exterior and an interior of said sample gas conduit;
    a diluted sample gas conduit disposed within said sample gas conduit having a mixing end with a mixing space inlet opening disposed proximate said sample gas inlet end forming an annular space between said sample gas conduit and said diluted sample gas conduit, said mixing end disposed at a distance from said sample gas flow restricting orifice;
    dilution gas means for introducing a dilution gas into said annular space;
    filter means for filtering said sample gas connected with said sample gas inlet end of said sample gas conduit; and
    a first tube disposed within said diluted sample gas conduit having a first tube inlet end disposed proximate said sample gas flow restricting orifice upstream of said mixing end of said diluted sample gas conduit.

2. An apparatus in accordance with claim 1 further comprising a second tube disposed within said diluted sample gas conduit having a second tube inlet end oriented toward said flow restricting orifice and at a distance downstream of said first tube inlet end.

3. An apparatus in accordance with claim 2, wherein said first tube and said second tube are capillary tubes.

4. An apparatus in accordance with claim 1, wherein said flow restricting orifice is a critical orifice.

5. An apparatus in accordance with claim 1, wherein said filter means comprises at least one porous wall enclosing a filtered gas chamber around said sample gas inlet end of said sample gas conduit.

6. An apparatus in accordance with claim 5 further comprising a purge/calibration conduit having a purge/calibration gas outlet end in fluid communication with said filtered gas chamber.

7. An apparatus for diluting a gas sample, the apparatus comprising:
    a sample gas conduit having a sample gas inlet end and a diluted sample gas outlet end;
    a first stage orifice plate forming a sample gas flow restricting orifice disposed proximate said sample gas inlet end connected with said sample gas conduit and providing fluid communication between an exterior and an interior of said sample gas conduit;
    a diluted sample gas conduit disposed within said sample gas conduit having a mixing end with a mixing space inlet opening disposed proximate said sample gas inlet end forming an annular space between said sample gas conduit and said diluted sample gas conduit, said mixing end disposed at a distance from said sample gas flow restricting orifice;
    dilution gas means for introducing a dilution gas into said annular space;
    filter means for filtering said sample gas connected with said sample gas inlet end of said sample gas conduit;
    a second stage orifice plate having a second stage flow restricting orifice disposed within and connected with said diluted sample gas conduit, said second stage flow restricting orifice axially aligned with said sample gas flow restricting orifice; and
    a first stage mixing space wall disposed in said diluted sample gas conduit between said sample gas flow restricting orifice and said second stage flow restricting orifice and forming a first stage offaxial flow mixing orifice and a first stage diluted sample gas chamber between said second stage flow restricting orifice and said first stage off-axial flow mixing orifice.

8. An apparatus in accordance with claim 7 further comprising a first tube disposed within said diluted sample gas conduit having a first tube inlet end disposed proximate said sample gas flow restricting orifice upstream of said mixing end of said diluted sample gas conduit.

9. An apparatus in accordance with claim 8, wherein said filter means comprises at least one porous wall enclosing a filtered gas chamber around said sample gas inlet end of said sample gas conduit.

10. An apparatus in accordance with claim 9 further comprising a purge/calibration conduit having a purge/calibration gas outlet end in fluid communication with said filtered gas chamber.

11. An apparatus in accordance with claim 7, wherein a second stage diluted sample gas conduit is disposed within said diluted sample gas conduit, said second stage diluted sample gas conduit having a second stage mixing end with a second stage mixing space wall disposed downstream of said second stage flow restricting orifice and forms a second annular space between said diluted sample gas conduit and said second stage diluted sample gas conduit, said second annular space in fluid communication with dilution gas means for introducing a dilution gas into said second annular space.

12. An apparatus in accordance with claim 11, wherein a third stage flow restricting orifice is disposed within and connected with said second stage diluted sample gas conduit, said third stage flow restricting orifice axially aligned with said sample gas flow restricting orifice, and a second stage mixing space wall is disposed in said second stage diluted sample gas conduit between said second stage flow restricting orifice and said third stage flow restricting orifice and forms a second stage off axial flow mixing orifice and a second stage diluted sample gas chamber between said third stage flow restricting orifice and said second stage off-axial flow mixing orifice.

13. An apparatus in accordance with claim 12, wherein a third stage diluted sample gas conduit is disposed within said second stage diluted sample gas conduit, said third stage diluted sample gas conduit having a third stage mixing end with a third stage mixing space wall disposed downstream of said third stage flow restricting orifice and forms a third annular space between said second stage diluted sample gas conduit and said third stage diluted sample gas conduit, said third annular space in fluid communication with dilution gas means for introducing said dilution gas into said third annular space.

14. An apparatus in accordance with claim 13, wherein a third stage mixing space wall is disposed in said third stage diluted sample gas conduit downstream of said third stage flow restricting orifice and forms a third stage off-axial flow mixing orifice.

* * * * *